(12) United States Patent
Mitsuhashi et al.

(10) Patent No.: US 12,303,108 B2
(45) Date of Patent: May 20, 2025

(54) ENDOSCOPE, DISTAL END PORTION OF ENDOSCOPE, AND INSERTION PORTION OF ENDOSCOPE

(71) Applicant: OLYMPUS CORPORATION, Tokyo (JP)

(72) Inventors: Keita Mitsuhashi, Hachioji (JP); Tsukasa Ota, Hachioji (JP); Takuto Yoshinaga, Hino (JP); Wataru Matsuura, Fuchu (JP); Motohiko Suzuki, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 395 days.

(21) Appl. No.: 17/835,210

(22) Filed: Jun. 8, 2022

(65) Prior Publication Data
US 2022/0296089 A1    Sep. 22, 2022

Related U.S. Application Data (63) Continuation of application No. PCT/JP2019/048801, filed on Dec. 12, 2019.

(51) Int. Cl.
*A61B 1/00* (2006.01)
*A61B 1/04* (2006.01)
*A61B 1/05* (2006.01)

(52) U.S. Cl.
CPC ............ *A61B 1/05* (2013.01); *A61B 1/00114* (2013.01); *A61B 1/00119* (2013.01); *A61B 1/04* (2013.01)

(58) Field of Classification Search
CPC ... A61B 1/05; A61B 1/00114; A61B 1/00119; A61B 1/00096; A61B 1/00097; A61B 1/051; A61B 1/04
See application file for complete search history.

(56) References Cited

U.S. PATENT DOCUMENTS 5,220,198 A * 6/1993 Tsuji .................. A61B 1/05
                                              257/E31.118
2009/0149713 A1    6/2009 Niida
(Continued)

FOREIGN PATENT DOCUMENTS

JP    2008-048905 A    3/2008
JP    2012-157472 A    8/2012
(Continued)

OTHER PUBLICATIONS

International Search Report dated Jan. 28, 2020 received in PCT/JP2019/048801.

*Primary Examiner* — Timothy J Neal
(74) *Attorney, Agent, or Firm* — Scully, Scott, Murphy & Presser, P.C.

(57) ABSTRACT

An endoscope includes an image pickup module having an optical axis that defines a visual field direction and provided with an electric contact, a cable that is disposed on a proximal end side of the image pickup module and transfers an image pickup signal generated by the image pickup module, a channel provided beside the image pickup module, and a movable board electrically connecting the electric contact and the cable to transfer the image pickup signal and including a movable portion capable of forming a curved surface that is freely displaceable in an optical axis direction. The movable portion of the movable board is arranged at a position where a distance between the curved surface and the channel is longer than a distance between the curved surface and the optical axis.

19 Claims, 5 Drawing Sheets

(56) References Cited

U.S. PATENT DOCUMENTS

2017/0007096 A1* 1/2017 Suzuki .................. A61B 1/051
2018/0317756 A1* 11/2018 Unsai ..................... H04N 23/54

FOREIGN PATENT DOCUMENTS

| JP | 2016-042961 A | 4/2016 |
| JP | 2017-074207 A | 4/2017 |
| WO | 2019/102679 A1 | 5/2019 |

* cited by examiner

ENDOSCOPE, DISTAL END PORTION OF ENDOSCOPE, AND INSERTION PORTION OF ENDOSCOPE

CROSS REFERENCE TO RELATED APPLICATION

This application is a continuation application of PCT/JP2019/048801 filed on Dec. 12, 2019, the entire contents of which are incorporated herein by this reference.

BACKGROUND OF THE INVENTION

1. Field of the Invention

The present invention relates to an endoscope, a distal end portion of an endoscope, and an insertion portion of an endoscope, and particularly relates to an endoscope including an image pickup module and a cable that transmits an image pickup signal from the image pickup module, a distal end portion of the endoscope, and an insertion portion of the endoscope.

2. Description of the Related Art

An endoscope system including an endoscope and a video processor or the like is widely used in, for example, medical and industrial fields, the endoscope being configured to pick up an image of an object inside a subject, the video processor or the like being configured to provide certain image processing to an observation image of the object picked up by the endoscope and output the observation image.

An endoscope used in such an endoscope system typically includes an elongated insertion portion that is inserted into a body cavity of a subject or the like. The insertion portion includes a rigid distal end portion provided on a distal end side, a bending portion that is freely bendable and provided at a rear end of the distal end portion, and an elongated flexible tube portion provided at a rear end of the bending portion.

Typically, an image pickup optical system and an image pickup device unit for image pickup of a subject are disposed in the above-described distal end portion of the insertion portion of the endoscope. Japanese Patent Application Laid-Open Publication No. 2016-042961 discloses an endoscope in which an image pickup cable for transmitting an image pickup signal from the above-described image pickup device unit is disposed on a proximal end side of such an image pickup device unit and a connection portion that connects the image pickup device unit and the image pickup cable is disposed.

In a structure used in a conventionally known example, the connection portion that connects the image pickup device unit and the image pickup cable as described above is sealed by, for example, resin.

In many known examples, a forceps channel that allows insertion of a treatment instrument is provided inside the insertion portion of the endoscope.

SUMMARY OF THE INVENTION

An endoscope according to an aspect of the present invention includes an image pickup module having an optical axis that defines a visual field direction and provided with an electric contact, a cable that is disposed on a proximal end side of the image pickup module and transfers an image pickup signal generated by the image pickup module, a channel provided beside the image pickup module, and a movable board electrically connecting the electric contact and the cable to transfer the image pickup signal and including a movable portion capable of forming a curved surface that is freely displaceable in an optical axis direction. The movable portion of the movable board is arranged at a position where a distance between the curved surface and the channel is longer than a distance between the curved surface and the optical axis. The endoscope further includes a first fixation member disposed at a position facing one end portion of the movable board, and a second fixation member disposed at a position facing another end portion of the movable board. The one end portion of the movable board has one surface fixed to the first fixation member and is sandwiched between the first fixation member and the electric contact of the image pickup module. The other end portion of the movable board has one surface fixed to the second fixation member and is sandwiched between the second fixation member and the cable.

A distal end portion of an endoscope according to another aspect of the present invention includes an image pickup module having an optical axis that defines a visual field direction, provided with an electric contact, and electrically connected to a cable that transfers an image pickup signal, a channel provided beside the image pickup module, and a movable board electrically connecting the electric contact and the cable to transfer the image pickup signal and including a movable portion capable of forming a curved surface that is freely displaceable in an optical axis direction. The movable portion of the movable board is arranged at a position where a distance between the curved surface and the channel is longer than a distance between the curved surface and the optical axis. The distal end portion further includes a first fixation member disposed at a position facing one end portion of the movable board, and a second fixation member disposed at a position facing another end portion of the movable board. The one end portion of the movable board has one surface fixed to the first fixation member and is sandwiched between the first fixation member and the electric contact of the image pickup module. The other end portion of the movable board has one surface fixed to the second fixation member and is sandwiched between the second fixation member and the cable.

An insertion portion of an endoscope according to another aspect of the present invention includes an image pickup module having an optical axis that defines a visual field direction and provided with an electric contact, a cable that is disposed on a proximal end side of the image pickup module and transfers an image pickup signal generated by the image pickup module, a channel provided beside the image pickup module, and a movable board electrically connecting the electric contact and the cable to transfer the image pickup signal and including a movable portion capable of forming a curved surface that is freely displaceable in an optical axis direction. The movable portion of the movable board is arranged at a position where a distance between the curved surface and the channel is longer than a distance between the curved surface and the optical axis. The insertion portion further includes a first fixation member disposed at a position facing one end portion of the movable board, and a second fixation member disposed at a position facing another end portion of the movable board. The one end portion of the movable board has one surface fixed to the first fixation member and is sandwiched between the first fixation member and the electric contact of the image pickup module. The other end portion of the movable board has one surface fixed to the second fixation member and is sandwiched between the second fixation member and the cable.

DETAILED DESCRIPTION OF THE PREFERRED EMBODIMENTS

Embodiments of the present invention will be described below with reference to the accompanying drawings.

Note that, in the drawings used in description below, a scale is changed for each constituent component in some cases to set a size in which the constituent component is recognizable in the drawing. The present invention is not limited to the number of constituent components, shapes of the constituent components, size ratios of the constituent components, and relative positional relations among the constituent components illustrated in the drawings.

First Embodiment

The following describes an endoscope according to a first embodiment of the present invention. In the present embodiment, the endoscope is assumed to be what is called a cholangioscope used for observation and medical treatment of inside of a bile duct (including inside of a common bile duct) or inside of a pancreatic duct. In the following description, the endoscope (cholangioscope) according to the present embodiment is assumed to be a baby endoscope applied to a mother endoscope in what is called a mother-baby endoscope system.

Figure 1:
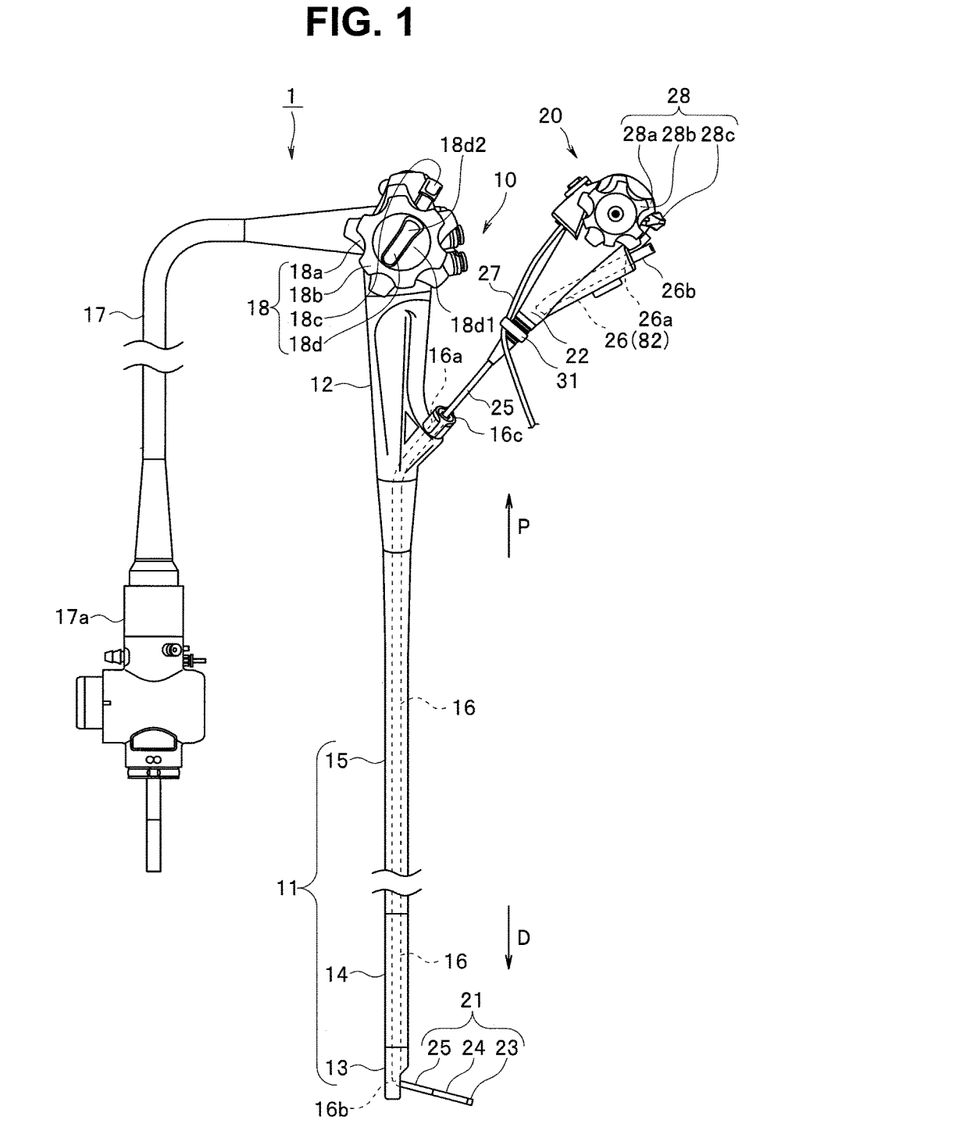
FIG. 1 is an exterior diagram illustrating an endoscope system including an endoscope (baby endoscope) according to a first embodiment of the present invention and a mother endoscope to which the baby endoscope is applied.

FIG. 1 is an exterior diagram illustrating an endoscope system 1 including an endoscope (baby endoscope) according to the first embodiment of the present invention and a mother endoscope to which the baby endoscope is applied. Note that, in FIG. 1 and other diagrams, an arrow P indicates a proximal end side (proximal end direction), and an arrow D indicates a distal end side (distal end direction).

A mother endoscope 10 in the endoscope system 1 according to the present embodiment illustrated in FIG. 1 is, for example, a duodenum endoscope, and a baby endoscope 20 as an endoscope of the present embodiment is a small-diameter endoscope that is inserted into a channel 26 of the mother endoscope 10. When the baby endoscope 20 is used for observation or medical treatment inside a bile duct (common bile duct) or a pancreatic duct, the baby endoscope 20 is protruded into a body cavity from a distal end portion of the mother endoscope 10 inserted into a duodenum and only the baby endoscope 20 is selectively inserted into the bile duct or the pancreatic duct from a duodenal papilla.

First, a configuration of the mother endoscope 10 in the endoscope system 1 will be described below. As illustrated in FIG. 1, the mother endoscope 10 includes an elongated shape insertion portion 11 that is inserted into a subject, and an operation portion 12 continuously provided on the proximal end side of the insertion portion 11. The operation portion 12 is provided with various operation members that are necessary for operating the mother endoscope 10.

The insertion portion 11 includes, sequentially from the distal end side toward the proximal end side, a distal end portion body 13, a bending portion 14, and a flexible tube portion 15, which are continuously provided.

For example, an illumination optical system configured to emit illumination light transmitted from a non-illustrated light guide bundle, an objective optical system, and an image pickup device are disposed in the distal end portion body 13 of the insertion portion 11. The image pickup device of the mother endoscope 10 is configured as, for example, a CCD image sensor or a CMOS image sensor.

The bending portion 14 of the insertion portion 11 is a first bending portion and bendable in all directions about an insertion axis, including, for example, up-down and right-left (U-D and R-L) directions.

The flexible tube portion 15 of the insertion portion 11 is configured as a flexible tubal member. For example, the channel 16, a non-illustrated image pickup cable, the light guide bundle, and an air-water feeding tube are disposed inside the flexible tube portion 15.

The channel 16 (in the mother endoscope 10) extends from the distal end portion body 13 of the insertion portion 11 to the operation portion 12. The channel 16 includes a proximal end side opening 16a on the distal end side of a bending operation portion 18 of the operation portion 12, which will be described later, and a distal end side opening 16b on the distal end portion body 13 of the insertion portion 11.

For example, a forceps plug 16c including a check valve (backflow prevention valve) is attached to the proximal end side opening 16a of the operation portion 12.

The channel 16 allows insertion of, through the forceps plug 16c, an insertion portion 21 of the baby endoscope 20 as an endoscope according to the present embodiment, and also allows insertion of another treatment instrument or the like.

The bending operation portion 18 for an operation to bend the bending portion 14 is provided on the proximal end side of the proximal end side opening 16a of the operation portion 12. The bending operation portion 18 includes a UD bending operation knob 18a, an RL bending operation knob 18b, a UD braking lever 18c, and an RL braking grip 18d. The RL braking grip 18d includes a disk portion 18d1, and a rectangular portion 18d2 protruding from the disk portion 18d1.

A universal cable 17 is extended from a side part of the operation portion 12 on the proximal end side. An endoscope connector 17a is provided at an extension end of the universal cable 17. When the endoscope connector 17a is connected to a non-illustrated external instrument (such as a processor or a light source device), a power source, a drive signal, illumination light, and the like are supplied to the mother endoscope 10 and a video picked up by the mother endoscope 10 is processed by the external instrument.

Description of Baby Endoscope 20

Figure 2:
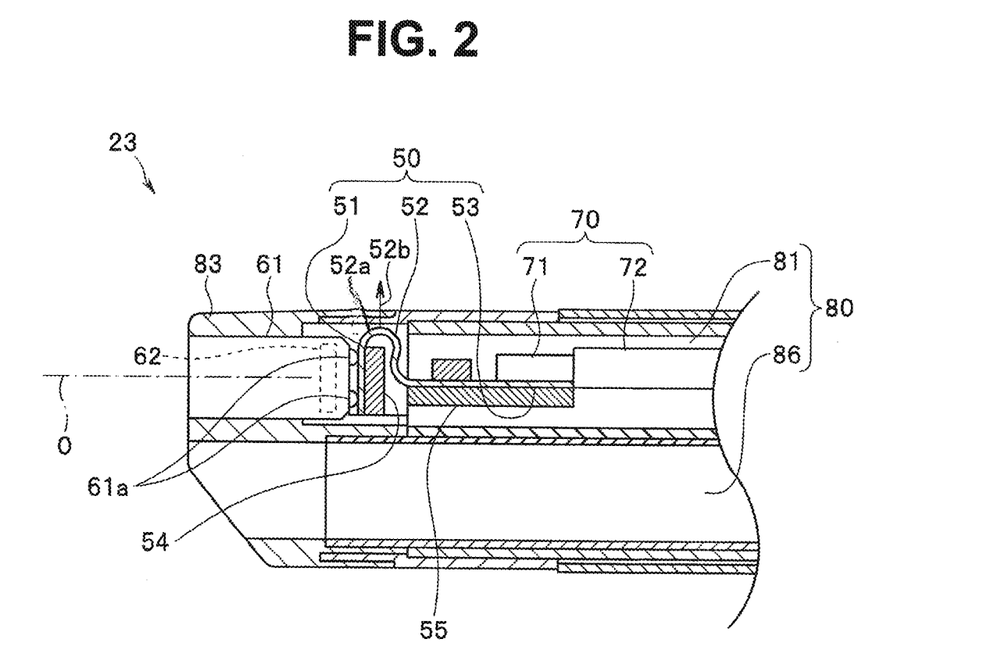
FIG. 2 is a main-part enlarged cross-sectional view illustrating an internal configuration of a distal end portion of an insertion portion of the endoscope according to the first embodiment.

Subsequently, the baby endoscope 20 as an endoscope of the present embodiment (cholangioscope) will be described below with reference to FIG. 2 in addition to FIG. 1. FIG. 2 is a main-part enlarged cross-sectional view illustrating an internal configuration of a distal end portion of the insertion portion of the endoscope according to the first embodiment.

As illustrated in FIG. 1, the baby endoscope 20 includes the insertion portion 21 having an elongated shape that allows insertion into the channel 16 of the mother endoscope 10, and an operation portion 22 continuously provided on the proximal end side of the insertion portion 21. Various operation members necessary for operating the baby endoscope 20 are disposed at the operation portion 22.

The insertion portion 21 includes a rigid distal end portion 23 provided on the distal end side, a bending portion 24 that is freely bendable and provided at a rear end of the distal end portion 23, and an elongated flexible tube portion 25 provided at a rear end of the bending portion 24.

As illustrated in FIG. 2, for example, an LED light source configured to generate illumination light (or having a configuration in which illumination light from a light source device is transmitted through a light guide) and an illumination optical system configured to emit the generated illumination light, which are not illustrated, and an image pickup module 61 in which an objective optical system and an image pickup device 62 are built are disposed at the distal end portion 23 of the insertion portion 21.

In the present embodiment, the image pickup device 62 is configured as a solid image pickup device such as a CCD image sensor or a CMOS image sensor. The image pickup module 61 is fixed to a distal frame part 83 of the distal end portion 23. An electric contact 61a for inputting a drive signal or the like to, for example, the image pickup device 62 is disposed on one end side of the image pickup module 61. Note that configurations of the image pickup device 62 and the image pickup module 61 will be described later in detail.

A distal end portion of an image pickup cable 70 that transfers an image pickup signal generated by the image pickup device 62 of the image pickup module 61 is disposed in the distal end portion 23. Note that the image pickup cable 70 is disposed on the proximal end side of the image pickup module 61. In addition, in the distal end portion 23, a channel 86 is provided beside the image pickup module 61 and allows insertion of a certain treatment instrument. The image pickup cable 70 and the channel 86 will be described later in detail.

The distal end portion 23 includes a movable board 50 electrically connecting the electric contact 61a of the image pickup module 61 with the image pickup cable 70 to transfer an image pickup signal from the image pickup device 62 and including a movable portion 52 capable of forming a curved surface 52a that is freely displaceable in an optical axis direction. Note that the movable board 50 will be described later in detail.

In FIG. 1, the bending portion 24 of the insertion portion 21 is bendable in all directions about the insertion axis, including, for example, the up-down and right-left (U-D and R-L) directions.

The flexible tube portion 25 of the insertion portion 21 is configured as a flexible tubal member. Inside the flexible tube portion 25, the channel 26 (denoted by reference sign 82 in the distal end portion 23; refer to FIG. 2) is formed, and in addition, for example, the image pickup cable 70 (refer to FIG. 2), an electric power line for an LED light source, and an air-water feeding tube are disposed. The flexible tube portion 25 has higher bending rigidity on the proximal end side than on the distal end side.

The channel 26 is a channel extending from the distal end portion 23 of the insertion portion 21 to the operation portion 22. The channel 26 has a proximal end side opening 26a at the operation portion 22 and has a non-illustrated distal end side opening at the distal end portion 23 of the insertion portion 21.

For example, a pipe sleeve 26b is provided at the proximal end side opening 26a of the operation portion 22.

A treatment instrument and the like can be inserted into the channel 26 through the pipe sleeve 26b. The channel 26 can be used to inject contrast dye and the like.

A bending operation portion 28 for an operation to bend the bending portion 24 is provided on the proximal end side of the operation portion 22. The bending operation portion 28 is a second bending operation portion including a UD bending operation knob 28a, an RL bending operation knob 28b, and a braking lever 28c. The UD bending operation knob 28a, the RL bending operation knob 28b, and the braking lever 28c are rotation operation members configured to be coaxially rotatable.

The UD bending operation knob 28a is a rotation operation member for an operation to bend the bending portion 24 in the up-down direction. The bending portion 24 bends in a U direction (up direction) when the UD bending operation knob 28a is rotated in one direction. The bending portion 24 bends in a D direction (down direction) when the UD bending operation knob 28a is rotated in the other direction.

The RL bending operation knob 28b is a rotation operation member for an operation to bend the bending portion 24 in the right-left direction. The bending portion 24 bends in an R direction (right direction) when the RL bending operation knob 28b is rotated in one direction. The bending portion 24 bends in an L direction (left direction) when the RL bending operation knob 28b is rotated in the other direction.

It is possible to perform bending in all directions about the insertion axis as described above by combining bending in the U-D direction through the UD bending operation knob 28a and bending in the R-L direction through the RL bending operation knob 28b.

The braking lever 28c is provided for braking operations to rotate the UD bending operation knob 28a and the RL bending operation knob 28b and configured to shift to a braking position at which rotation is braked and an open position at which rotation is not braked. The braking lever 28c is configured to perform braking using, for example, frictional force. With the braking lever 28c, it is possible not only to restrict rotation of the UD bending operation knob 28a and the RL bending operation knob 28b but also to finely adjust rotational positions by controlling braking force, as described above.

A cable/tube 27 is extended from the proximal end side of the operation portion 22 (note that although only one cable/tube is illustrated for simplification, a plurality of cables/ tubes may be provided). The cables/tubes 27 include cables such as an image pickup cable and a power supply cable, an air-water feeding tube, and a suction tube and are connected to an external instrument (for example, a processor (refer to FIG. 3) or an air-water feeding device). The cables/tubes 27 are locked to, for example, a bending stopper on the distal end side of the operation portion 22 through a holder 31 such as a clip, a band, or a strap.

A connection relation between a baby endoscope connector disposed at distal end portions of image pickup, power supply, and illumination light supply cables among the cables/tubes 27 described above and a processor to which the baby endoscope connector is connected will be described below with reference to FIGS. 3 and 4.

Figure 3:
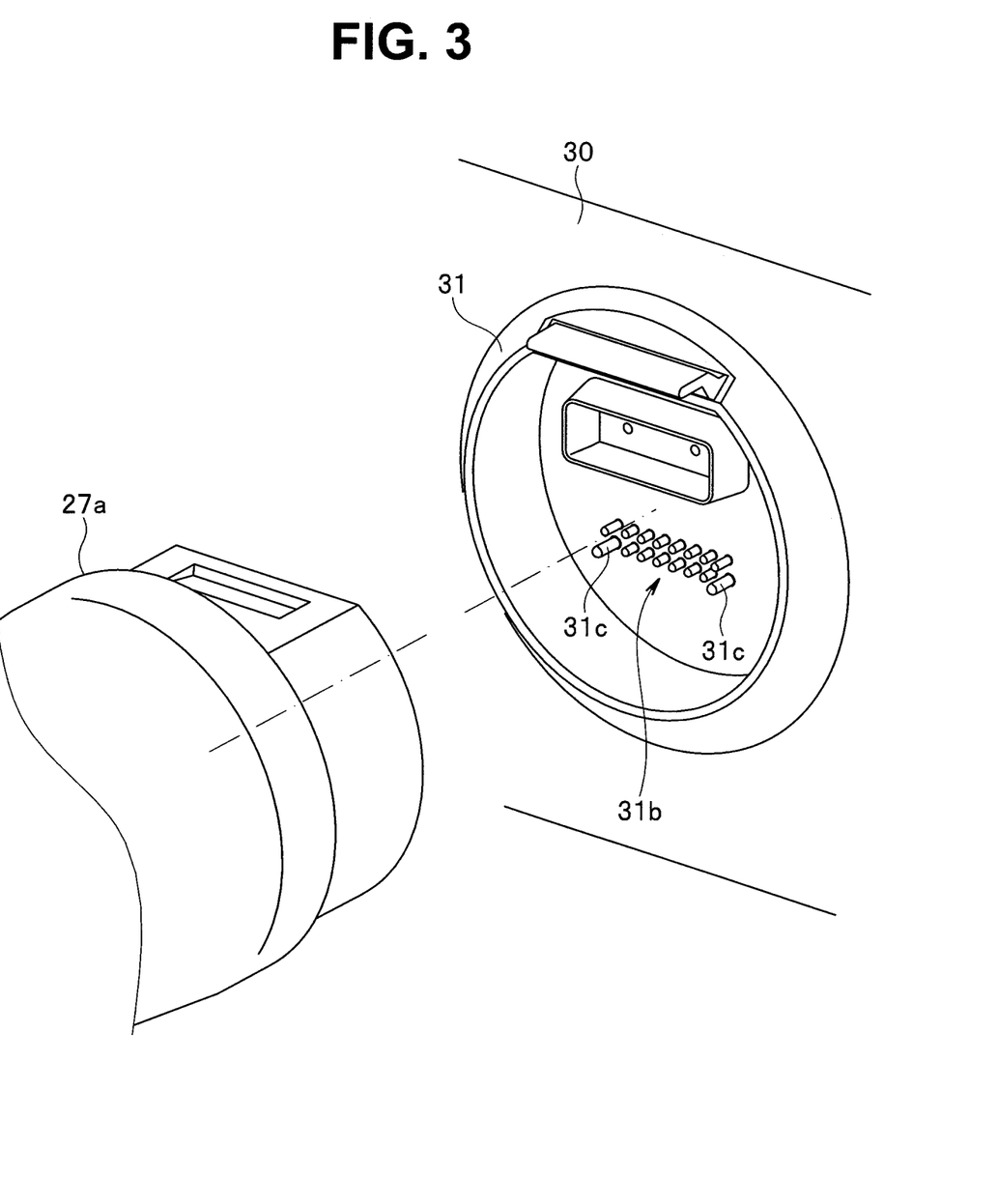
FIG. 3 is a perspective view illustrating a connection relation between a baby endoscope connector extended from the endoscope according to the first embodiment and a video processor.

FIG. 3 is a perspective view illustrating a connection relation between a baby endoscope connector extended from the endoscope according to the first embodiment and a video processor. FIG. 4 is a perspective view illustrating a distal end surface of the baby endoscope connector.

Figure 4:
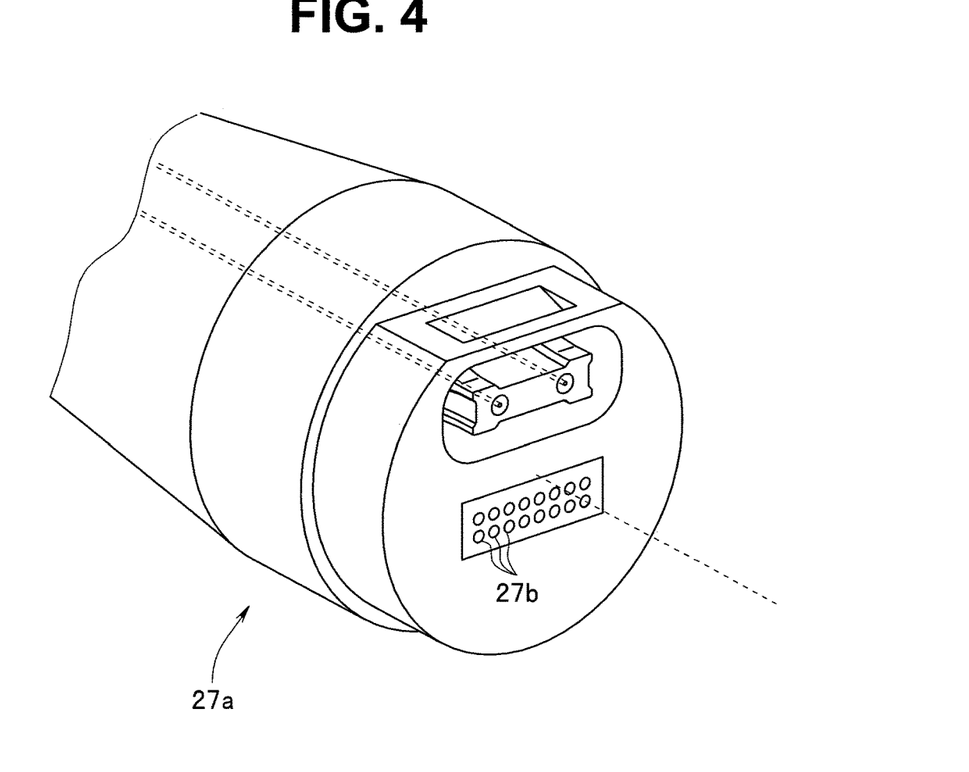
FIG. 4 is a perspective view illustrating a distal end surface of the baby endoscope connector extended from the endoscope according to the first embodiment.

As illustrated in FIGS. 3 and 4, a baby endoscope connector 27a is connected to a receptacle 31 provided to a processor 30. As illustrated in FIG. 4, a plurality of electric contacts 27b are disposed at a distal end surface of the baby endoscope connector 27a. A plurality of connection pins 31b are arranged at the receptacle 31 of the processor 30. When the baby endoscope connector 27a is connected to the receptacle 31, the plurality of electric contacts 27b of the baby endoscope connector 27a are connected to the plurality of corresponding connection pins 31b of the receptacle 31. Accordingly, certain power supply is performed from the processor 30 to the baby endoscope 20, and a certain image pickup signal is transmitted from the baby endoscope 20 to the processor 30.

Each connection pin 31b of the receptacle 31 is configured as a movable probe pin having a distal end that extends and contracts and typically referred to as a pogo pin, a spring pin, or the like. In the present embodiment, one or a plurality of ground pins 31c (refer to FIG. 3) as part of the plurality of connection pins 31b protrude farther than the other pins in an opening direction of the receptacle 31.

For example, as illustrated in FIG. 3, the plurality of connection pins 31b are all configured as pogo pins of the same kind, and the ground pins 31c are each configured as a pogo pin that has a distal end portion covered with a conductive member and accordingly protrudes farther than the other connection pins. Note that protruding pins are not limited to the ground pins 31c but may include power source pins, and accordingly, ground pins, power source pins, and other pins may have desired heights.

With the above-described configuration of the connection pins 31b including the ground pins 31c, for example, the ground pins 31c are connected first, and subsequently, the other pins are connected when the baby endoscope connector 27a is connected to the receptacle 31. Accordingly, for example, when the baby endoscope connector 27a of the baby endoscope 20 is connected to the receptacle 31 while the processor 30 is powered on, ground potential of electric circuits of the image pickup device 62 of the baby endoscope 20 can be maintained at zero potential (0V) through the ground pins 31c. Thus, it is possible to reliably operate a power source of the image pickup device 62 as well as various signals such as an image pickup signal and a communication signal.

When the baby endoscope connector 27a is removed from the receptacle 31, connection of the ground pins 31c is canceled after connection of the other connection pins, and thus the removal can be performed while the electric circuits of the image pickup device 62 are stabilized. Note that, in addition to the above-described configuration, diameters of the ground pins 31c may be larger than diameters of the other pins.

Configuration Inside Distal End Portion 23

Figure 5:
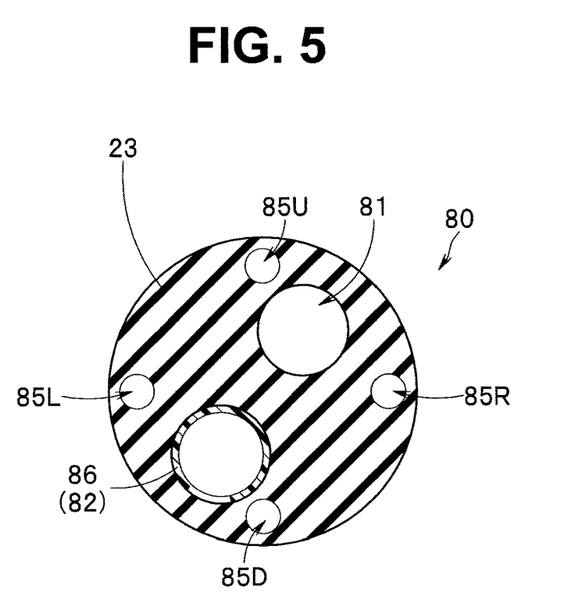
FIG. 5 is a main-part enlarged cross-sectional view illustrating a section orthogonal to a longitudinal axis of the distal end portion of the insertion portion of the endoscope according to the first embodiment.

Subsequently, the internal configuration of the distal end portion 23 of the insertion portion 21 of the baby endoscope 20 will be described below with reference to FIG. 5 in addition to FIG. 2. FIG. 5 is a main-part enlarged cross-sectional view illustrating a section orthogonal to a longitudinal axis of the distal end portion of the insertion portion of the endoscope according to the first embodiment.

As illustrated in FIG. 2, a flexible multiple-lumen tube 80 in which a plurality of lumina are formed is disposed in the distal end portion 23 of the insertion portion 21 of the baby endoscope 20.

As illustrated in FIG. 5, an observation optical system lumen 81 and a treatment instrument insertion lumen 82 as well as bending operation lumina 85U. 85D, 85L, and 85R are formed in the multiple-lumen tube 80.

The distal end portion of the image pickup cable 70 extended in the insertion portion 21 is inserted into the observation optical system lumen 81, and the image pickup module 61 is disposed on the distal end side of the observation optical system lumen 81. An interior tube is disposed on an inner surface of the treatment instrument insertion lumen 82 and functions as a channel 86.

The bending operation lumina 85U, 85D, 85L, and 85R are an upward pulling wire insertion lumen, a downward pulling wire insertion lumen, a leftward pulling wire insertion lumen, a rightward pulling wire insertion lumen, respectively.

When assembled to the distal end portion 23, the image pickup module 61 is fixed to the distal frame part 83 disposed on the distal end side of the distal end portion 23. The distal frame part 83 is formed of a rigid member and is formed of a member that is more rigid than at least the multiple-lumen tube 80 described above.

Note that the channel 86 described above in the present embodiment is arranged at a position beside the image pickup module 61. Specifically, the treatment instrument insertion lumen 82 (in which the channel 86 is provided) as a lumen in the multiple-lumen tube 80 is provided at a close position beside the observation optical system lumen 81 as a lumen in the multiple-lumen tube 80. This means that a space in the treatment instrument insertion lumen 82 is positioned close to the image pickup cable 70 disposed in the observation optical system lumen 81.

The image pickup module 61 includes a non-illustrated objective optical system including a lens through which an object image is incident, and the image pickup device 62 disposed at an imaging position of the objective optical system. When assembled to the distal end portion 23, the image pickup module 61 is disposed so that an axis of the image pickup module 61 aligns with an optical axis that defines a visual field direction of the insertion portion of the endoscope. In addition, the electric contact 61a for inputting a drive signal or the like to, for example, the image pickup device 62 is disposed on one end side of the image pickup module 61.

In the present embodiment, the image pickup device 62 is configured as a solid image pickup device such as a CCD image sensor or a CMOS image sensor. In the present embodiment, the image pickup device 62 is arranged at a position where an image pickup surface of the image pickup device 62 is orthogonal to an axis of the objective optical system. The image pickup device 62 is driven by a certain drive signal inputted through the electric contact 61*a*, photoelectrically converts an incident subject image, and outputs the subject image toward a component at a later stage.

As illustrated in FIG. 2, the image pickup cable 70 includes a cable body 72 (covering member) and an electric contact portion 71 (core wire portion) formed at a distal end portion of the cable body 72, extends in the flexible tube portion 25 of the insertion portion 21, and transfers an image pickup signal generated by the image pickup device 62 of the image pickup module 61. The distal end portion of the image pickup cable 70 is inserted into the observation optical system lumen 81 of the multiple-lumen tube 80, and the electric contact portion 71 formed at the distal end portion is connected to an electric contact portion formed at a proximal end side end portion 53 of the movable board 50.

The movable board 50 that electrically connects the electric contact 61*a* of the image pickup module 61 with the electric contact portion 71 of the image pickup cable 70 and transfers an image pickup signal from the image pickup device 62 is disposed in the distal end portion 23.

Configuration of Movable Board 50

The movable board 50 connecting the image pickup module 61 and the image pickup cable 70 will be described below with reference to FIG. 6 in addition to FIG. 2.

Figure 6:
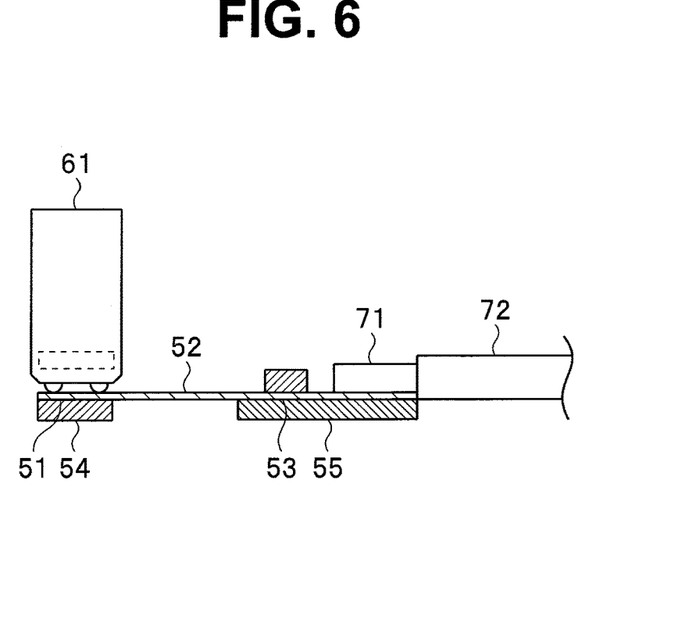
FIG. 6 is a sectional side view illustrating a state before a movable board for connecting an image pickup module disposed at the distal end portion of the insertion portion of the endoscope according to the first embodiment with an image pickup cable is assembled to the distal end portion of the insertion portion.

FIG. 6 is a sectional side view illustrating a state before the movable board 50 for connecting the image pickup module 61 disposed in the distal end portion of the insertion portion of the endoscope according to the first embodiment with the image pickup cable 70 is assembled to the distal end portion 23 of the insertion portion. In this manner, FIG. 6 illustrates a state before the movable board 50 connecting the image pickup module 61 and the image pickup cable 70 is assembled in the distal end portion 23, whereas FIG. 2 illustrates a state after the image pickup module 61, the image pickup cable 70, and the movable board 50 are assembled in the distal end portion 23.

The movable board 50 is a thin-plate flexible circuit board that is freely displaceable at least in the optical axis direction. The movable board 50 includes one end portion 51 connected to the electric contact 61*a* of the image pickup module 61, another end portion 53 connected to the electric contact portion 71 of the image pickup cable 70, and the movable portion 52 that is a portion between the one end portion 51 and the other end portion 53 and freely displaceable in the optical axis direction.

When assembled in the distal end portion 23, the movable portion 52 forms the curved surface 52*a* that is freely displaceable in the optical axis direction between the one end portion 51 and the other end portion 53. The curved surface 52*a* will be described later in detail. Note that no electric components are mounted on the curved surface 52*a* in the present embodiment, but electric components may be mounted on a small-curvature part of the curved surface 52*a*.

In the present embodiment, a first fixation member 54 is fixed to one surface of the one end portion 51 of the movable board 50 and reinforces strength of the one end portion 51. In addition, a second fixation member 55 is fixed to one surface of the other end portion 53 and reinforces strength of the other end portion 53.

Before being assembled to the distal end portion 23, the movable board 50 including the movable portion 52 is stretched substantially straight in a longitudinal direction of the movable board 50 as illustrated in FIG. 6. In this state, the one end portion 51 is connected to the electric contact 61*a* of the image pickup module 61. In this state, the one end portion 51 with the one surface being fixed to the first fixation member 54 is sandwiched between the first fixation member 54 and the electric contact 61*a* of the image pickup module 61. Note that, in this case, the image pickup module 61 is disposed in a direction that an axial direction of the image pickup module 61 (axial direction of the included objective optical system) is orthogonal to a stretching direction of the movable board 50.

Similarly, the other end portion 53 is connected to the electric contact portion 71 of the image pickup cable 70 while the movable board 50 is stretched substantially straight in the longitudinal direction. In this state, the other end portion 53 with the one surface being fixed to the second fixation member 55 is sandwiched between the second fixation member 55 and the image pickup cable 70. Accordingly, the image pickup module 61 and the image pickup cable 70 are electrically connected to each other through the movable board 50 so that an image pickup signal from the image pickup device 62 can be transferred to a component at a later stage.

As described above, FIG. 2 illustrates a state after the image pickup module 61 and the image pickup cable 70 connected to each other through the movable board 50 are assembled in the distal end portion 23.

As illustrated in FIG. 2, when assembled in the distal end portion 23, the image pickup module 61 is arranged in an orientation that the axial direction of the included objective optical system aligns with the optical axis that defines the visual field direction of the insertion portion of the endoscope. The image pickup module 61 is also fixed to the rigid distal frame part 83 on the distal end side of the distal end portion 23. Note that the distal frame part 83 is formed of a member that is more rigid than at least the multiple-lumen tube 80 as described above.

In the distal end portion 23, the image pickup cable 70 is arranged at a substantially defined position in the optical axis direction. Thus, a position of the electric contact portion 71 of the image pickup cable 70 in the optical axis direction is substantially defined in the distal end portion 23.

A distance between the electric contact 61*a* of the image pickup module 61 and the electric contact portion 71 of the image pickup cable 70 in the optical axis direction when the image pickup module 61 and the image pickup cable 70 are assembled in the distal end portion 23 is set to be shorter than in the state in which the movable board 50 is stretched substantially straight as illustrated in FIG. 6.

Accordingly, when assembled to the distal end portion 23, the movable board 50 connected to the image pickup module 61 and the image pickup cable 70 is housed in a space formed on a front side of the observation optical system lumen 81 while the curved surface 52*a* is formed by the movable portion 52 that is freely displaceable.

In particular, since the one end portion 51 and the other end portion 53 of the movable board 50 are reinforced by the first fixation member 54 and the second fixation member 55, respectively, in the present embodiment, a curved portion such as the above-described curved surface 52*a* is reliably formed at the movable portion 52 positioned between the one end portion 51 and the other end portion 53.

In this manner, the movable board 50 connecting the image pickup module 61 and the image pickup cable 70 is provided with the movable portion 52 that is freely displaceable at least in the optical axis direction, and the image pickup module 61 connected to one end of the movable board 50 is fixed to the distal frame part 83 of the distal end portion 23. Accordingly, the image pickup cable 70 connected to the other end of the movable board 50 can have a certain freedom.

Moreover, as described above, in the movable board 50 according to the present embodiment, the curved surface 52a formed at the movable portion 52 is arranged in a direction in which a normal 52b of a maximum curvature surface of the curved surface 52a is substantially orthogonal to an optical axis O, in other words, at a position at which the maximum curvature surface faces a side of the distal end portion 23 and the curved surface 52a is separated from the optical axis O as illustrated in FIG. 2. This arrangement is achieved when such positioning is made that a distance between the curved surface 52a and a central axis of the distal end portion 23 is longer than a distance between the curved surface 52a and the optical axis O. In other words, the arrangement is achieved when such positioning is made that a distance between the curved surface 52a and the channel 86 is longer than the distance between the curved surface 52a and the optical axis O.

The movable board 50 according to the present embodiment is formed so that a width of the curved surface 52a formed at the movable portion 52 (width in a direction orthogonal to the longitudinal direction of the movable board 50) is smaller than widths of the first fixation member 54 and the second fixation member 55. Accordingly, the movable board 50 is more easily deformable.

In this manner, since the curved surface 52a is formed in the above-described direction (faces in the direction in which the normal 52b of the maximum curvature surface is substantially orthogonal to the optical axis O) and arranged at the position separated from the optical axis O, it is possible to reduce influence of some external force applied to the image pickup cable 70 or the movable board 50.

In particular, since the channel 86 is provided at a close position beside the image pickup module 61 and the image pickup cable 70, the distal end portion 23 in the present embodiment as described above is prone to influence of, for example, a treatment instrument inserted into the channel 86. However, when external force is applied from the treatment instrument or the like, the applied external force can be absorbed by the movable portion 52 forming the curved surface 52a.

As described above, with a configuration of the present embodiment, the image pickup module 61 and the image pickup cable 70 are connected by the movable board 50 including the movable portion 52 that is displaceable as described above, and accordingly, the image pickup cable 70 can be movably supported in the distal end portion 23 and external force application can be absorbed by the movable portion 52. Thus, when unexpected external force is applied from, for example, a treatment instrument inserted in the channel 86, it is possible to reduce influence of the application on electric circuits such as the image pickup module 61 and the image pickup cable 70 as much as possible, thereby preventing defects such as image anomaly.

Moreover, it is possible to achieve simple assembly without interference at channel assembly at the distal end portion of the insertion portion or assembly of a bending pipe.

Second Embodiment

Subsequently, an endoscope according to a second embodiment of the present invention will be described below. Note that, similarly to the first embodiment, the endoscope according to the second embodiment is assumed to be what is called a cholangioscope and assumed to be a baby endoscope applied to a mother endoscope in a mother-baby endoscope system.

Specifically, the endoscope according to the second embodiment is different from the first embodiment in arrangement orientations of the image pickup module 61, the movable board 50, and the image pickup cable 70 in the distal end portion of the insertion portion. The other configuration is same as in the first embodiment, and thus only the difference from the first embodiment will be described below, and description of any common part is omitted.

Description of Baby Endoscope 20 in Second Embodiment

Figure 7:
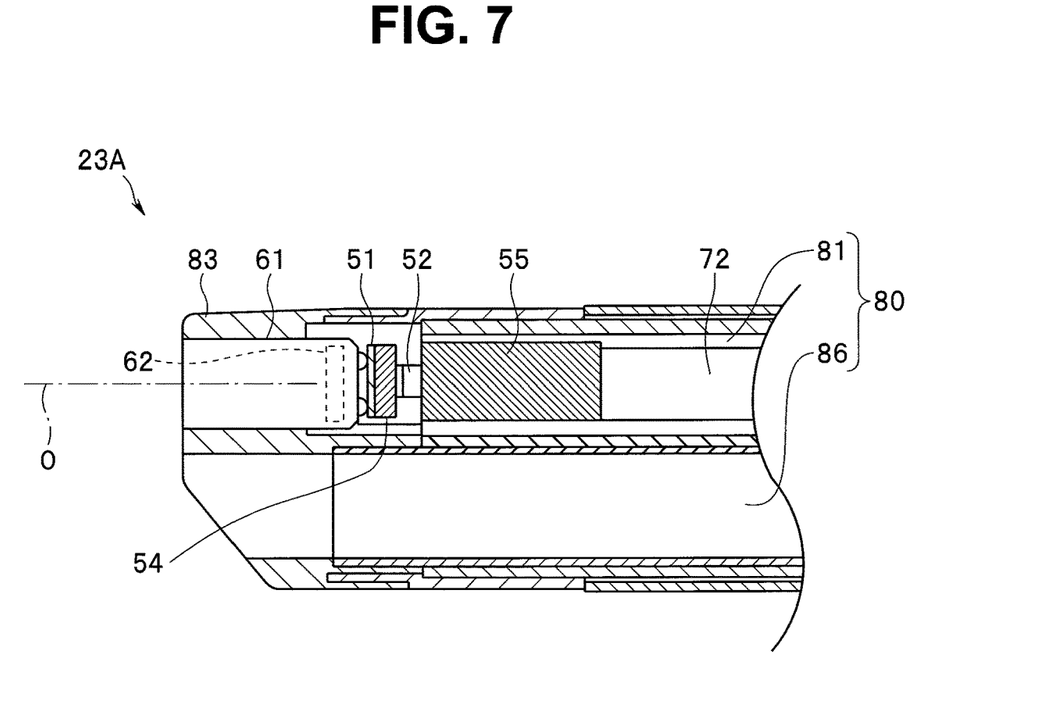
FIG. 7 is a main-part enlarged cross-sectional view illustrating an internal configuration of a distal end portion of an insertion portion of an endoscope according to a second embodiment.

FIG. 7 is a main-part enlarged cross-sectional view illustrating an internal configuration of the distal end portion of the insertion portion of the endoscope according to the second embodiment.

In the second embodiment, similarly to the first embodiment, the baby endoscope 20 includes the insertion portion 21 having an elongated shape that allows insertion into the channel 16 of the mother endoscope 10, and the operation portion 22 continuously provided on the proximal end side of the insertion portion 21.

The insertion portion 21 in the baby endoscope 20 according to the second embodiment includes a rigid distal end portion 23A provided on the distal end side, the bending portion 24 that is freely bendable and provided at a rear end of the distal end portion 23A, and the elongated flexible tube portion 25 provided at a rear end of the bending portion 24.

In the second embodiment as well, the flexible multiple-lumen tube 80 in which a plurality of lumina are formed are disposed in the distal end portion 23A of the insertion portion 21 of the baby endoscope 20 as illustrated in FIG. 7. The distal end portion of the image pickup cable 70 extended in the insertion portion 21 is inserted into the observation optical system lumen 81 in the multiple-lumen tube, and the image pickup module 61 is disposed on the distal end side of the observation optical system lumen 81. In addition, similarly to the first embodiment, the treatment instrument insertion lumen 82 as another lumen in the multiple-lumen tube 80 is formed in the distal end portion 23A.

In the second embodiment as well, the image pickup module 61, the movable board 50, and the image pickup cable 70 have configurations same as in the first embodiment. For example, at a stage before assembly to the distal end portion 23A, the image pickup module 61, the movable board 50, and the image pickup cable 70 have the same connection relation as in the first embodiment as illustrated in FIG. 4.

However, in the second embodiment, when assembled to the distal end portion 23A, the image pickup module 61, the movable board 50, and the image pickup cable 70 are arranged at positions rotated about the axis by 90° relative to positions in the first embodiment as illustrated in FIG. 3.

Specifically, similarly to the first embodiment, when fixed to the distal frame part 83 of the distal end portion 23A, the image pickup module 61 is arranged at a position rotated about the axis by 90°. Similarly to the image pickup module 61, the movable board 50 and the image pickup cable 70 connected to the image pickup module 61 are arranged at positions rotated about the axis by 90°.

In the second embodiment as well, similarly to the first embodiment, the movable portion 52 of the movable board 50 forms the curved surface 52a. Specifically, when assembled in the distal end portion 23A, the movable portion 52 forms the curved surface 52a that is freely displaceable in the optical axis direction between the one end portion 51 and the other end portion 53.

In the second embodiment as well, the first fixation member 54 is fixed to one surface of the one end portion 51 of the movable board 50 and reinforces the strength of the one end portion 51, and the second fixation member 55 is fixed to one surface of the other end portion 53 and reinforces the strength of the other end portion 53.

Accordingly, in the second embodiment as well, when assembled to the distal end portion 23A, the movable board 50 connected to the image pickup module 61 and the image pickup cable 70 is housed in the space formed on the front side of the observation optical system lumen 81 while the curved surface 52a is formed by the movable portion 52 that is freely displaceable.

In the second embodiment as well, although hidden in FIG. 3, the curved surface 52a formed at the movable portion 52 is arranged at the position at which the normal 52b of the maximum curvature surface of the curved surface 52a is substantially orthogonal to the optical axis O and the curved surface 52a is separated from the optical axis O.

In this manner, in the second embodiment as well, the movable board 50 connecting the image pickup module 61 and the image pickup cable 70 is provided with the movable portion 52 that is freely displaceable at least in the optical axis direction, and the image pickup module 61 connected to one end of the movable board 50 is fixed to the distal frame part 83 of the distal end portion 23A. Accordingly, the image pickup cable 70 connected to the other end of the movable board 50 can have a certain freedom.

Since the curved surface 52a is formed in the above-described direction (faces in the direction in which the normal 52b of the maximum curvature surface is substantially orthogonal to the optical axis O) and arranged at the position separated from the optical axis O, it is possible to reduce influence of some external force applied to the image pickup cable 70 or the movable board 50.

As described above, with a configuration of the second embodiment as well, similarly to the first embodiment, the image pickup module 61 and the image pickup cable 70 are connected by the movable board 50 including the movable portion 52 that is displaceable as described above, and accordingly, the image pickup cable 70 can be movably supported in the distal end portion 23A and external force application can be absorbed by the movable portion 52. Thus, when unexpected external force is applied from, for example, a treatment instrument inserted in the channel 86, it is possible to reduce influence of the application on electric circuits such as the image pickup module 61 and the image pickup cable 70 as much as possible, thereby preventing defects such as image anomaly.

Moreover, it is possible to achieve simple assembly without interference at channel assembly at the distal end portion of the insertion portion or assembly of a bending pipe.

The present invention is not limited to the above-described embodiments but may be, for example, changed or modified in various manners without departing from the gist of the present invention. For example, a baby endoscope applied to a mother endoscope in a mother-baby endoscope system is assumed in the first and second embodiments, but the baby endoscope may be replaced with a treatment instrument (for example, biopsy forceps) provided with an image pickup apparatus. In this case, the image pickup module and the image pickup cable in the first and second embodiments may be connected through the movable board to a configuration of the image pickup apparatus provided to the treatment instrument. With this configuration, when the image pickup apparatus of the treatment instrument suffers stress due to, for example, deformation of a body of the treatment instrument (for example, biopsy forceps), it is possible to reduce influence of the stress on electric circuits such as the image pickup module and the image pickup cable as much as possible.

What is claimed is:

1. An endoscope comprising:
   an image sensor intersecting an optical axis and the image sensor having an electric contact;
   a cable configured to transfer an image pickup signal generated by the image sensor;
   a channel provided adjacent to the image sensor; and
   a board electrically connecting the electric contact and the cable, the board including a movable portion having a curved surface movable in an optical axis direction, wherein
   the movable portion is arranged at a position where a distance between the curved surface and the channel is longer than a distance between the curved surface and the optical axis,
      a first fixation member disposed at a first position facing a first end portion of the board, and
      a second fixation member disposed at a second position facing a second end portion of the board,
   wherein the first end portion has a first surface fixed to the first fixation member and is sandwiched between the first fixation member and the electric contact of the image sensor, and
   the second end portion has a second surface fixed to the second fixation member and is sandwiched between the second fixation member and the cable.

2. The endoscope according to claim 1, wherein an image pickup surface of the image sensor is positioned orthogonal to the optical axis.

3. The endoscope according to claim 1, further comprising:
   a flexible multiple-lumen tube having a first lumen,
   wherein the cable is disposed in the first lumen, and
   the image sensor is disposed on a distal end side of the first lumen and fixed to a distal end portion that is more rigid than the flexible multiple-lumen tube.

4. The endoscope according to claim 1, wherein the movable portion of the board has a first width in a direction orthogonal to a longitudinal direction smaller than a second width of another portion of the board, other than the movable portion, in the direction orthogonal to the longitudinal direction.

5. The endoscope according to claim 1, further comprising an image pickup module, the image pickup module comprising the image sensor, the image pickup module being disposed in the distal end portion.

6. The endoscope according to claim 1, wherein
   the channel comprises a first channel;
   the endoscope comprises a second channel, the board being disposed in the second channel; and
   a normal direction of an apex of the curved surface is oriented in a direction between centers of the first and second channels.

7. The endoscope according to claim 1, wherein
   the channel comprises a first channel;
   the endoscope comprises a second channel, the board being disposed in the second channel; and a normal direction of an apex of the curved surface is oriented orthogonally relative to a direction between centers of the first and second channels.

8. A distal end portion for use with an endoscope, the distal end portion comprising:
an image sensor having an optical axis-and an electric contact electrically connected to a cable configured to transfer an image pickup signal from the image sensor;
a channel provided adjacent to the image pickup module; and
a board electrically connecting the electric contact and the cable, the board including a movable portion having a curved surface movable in an optical axis direction, wherein
the movable portion is arranged at a position where a distance between the curved surface and the channel is longer than a distance between the curved surface and the optical axis,
the distal end portion further includes a first fixation member disposed at a first position facing a first end portion of the board, and a second fixation member disposed at a second position facing a second end portion of the board,
the first end portion has a first surface fixed to the first fixation member and is sandwiched between the first fixation member and the electric contact of the image sensor, and
the second end portion has a second surface fixed to the second fixation member and is sandwiched between the second fixation member and the cable.

9. The distal end portion according to claim 8, wherein an image pickup surface of the image sensor is positioned orthogonal to the optical axis.

10. The distal end portion according to claim 8, further comprising:
a flexible multiple-lumen tube having a first lumen,
wherein the cable is disposed in the first lumen, and
the image sensor is disposed on a distal end side of the first lumen and fixed to a distal end portion that is more rigid than the flexible multiple-lumen tube.

11. The distal end portion according to claim 8, wherein the movable portion of the board has a first width in a direction orthogonal to a longitudinal direction smaller than a second width of another portion of the board, other than the movable portion, in the direction orthogonal to the longitudinal direction.

12. An insertion portion for use with an endoscope, the insertion portion comprising:
the distal end portion according to claim 8.

13. The insertion portion according to claim 12, wherein an image pickup surface of the image sensor is positioned orthogonal to the optical axis.

14. The insertion portion according to claim 12, further comprising:
a flexible multiple-lumen tube having a first lumen,
wherein the cable is disposed in the first lumen, and
the image sensor is disposed on a distal end side of the first lumen and fixed to a distal end portion that is more rigid than the flexible multiple-lumen tube.

15. The insertion portion according to claim 12, wherein the movable portion of the board has a first width in a direction orthogonal to a longitudinal direction smaller than a second width of another portion of the board, other than the movable portion, in the direction orthogonal to the longitudinal direction.

16. The insertion portion according to claim 12, further comprising an image pickup module, the image pickup module comprising the image sensor, the image pickup module being disposed in the distal end portion.

17. The insertion portion according to claim 12, wherein the channel comprises a first channel;
the endoscope comprises a second channel, the board being disposed in the second channel; and
a normal direction of an apex of the curved surface is oriented in a direction between centers of the first and second channels.

18. The insertion portion according to claim 12, wherein the channel comprises a first channel;
the endoscope comprises a second channel, the board being disposed in the second channel; and
a normal direction of an apex of the curved surface is oriented orthogonally relative to a direction between centers of the first and second channels.

19. The distal end portion according to claim 8, further comprising an image pickup module, the image pickup module comprising the image sensor, the image pickup module being disposed in the distal end portion.

* * * * *